(12) United States Patent
Henneberg et al.

(10) Patent No.: US 11,160,799 B2
(45) Date of Patent: Nov. 2, 2021

(54) PEDIATRIC COMBINATION

(71) Applicant: Cessatech A/S, Copenhagen (DK)

(72) Inventors: Steen Henneberg, Copenhagen (DK); Bettina Nygaard Nielsen, Copenhagen (DK)

(73) Assignee: Cessatech A/S, Copenhagen (DK)

( * ) Notice: Subject to any disclaimer, the term of this patent is extended or adjusted under 35 U.S.C. 154(b) by 0 days.

(21) Appl. No.: 17/017,988

(22) Filed: Sep. 11, 2020

(65) Prior Publication Data
US 2021/0113546 A1    Apr. 22, 2021

(30) Foreign Application Priority Data
Oct. 22, 2019    (EP) .................... 19204617

(51) Int. Cl.
| | | |
|---|---|---|
| A61K 31/4535 | (2006.01) | |
| A61K 9/00 | (2006.01) | |
| A61K 31/135 | (2006.01) | |

(52) U.S. Cl.
CPC ........ *A61K 31/4535* (2013.01); *A61K 9/0043* (2013.01); *A61K 9/0073* (2013.01); *A61K 31/135* (2013.01)

(58) Field of Classification Search
CPC .............. A61K 31/4535; A61K 9/0043; A61K 9/0073; A61K 31/135
See application file for complete search history.

(56) References Cited

U.S. PATENT DOCUMENTS

| | | | |
|---|---|---|---|
| 6,825,203 B2 | 11/2004 | Pasternak et al. | |
| 2004/0092531 A1* | 5/2004 | Chizh ................ | A61K 2300/00 514/255.05 |
| 2007/0248548 A1* | 10/2007 | Blondino ............... | A61K 38/28 424/44 |
| 2014/0275276 A1* | 9/2014 | Basstanie ............ | A61K 31/135 514/646 |
| 2018/0296850 A1* | 10/2018 | Wang ................. | A61K 41/0052 |

OTHER PUBLICATIONS

Nielsen (Year: 2014).*
Blount, et al., "Pediatric Procedural Pain", Behav Modif, 2006, pp. 24-49; 26 pages.
Hadley, et al., "A survey of intranasal medication use in the paediatric emergency setting in England and Wales", Emerg Med J, 2010, pp. 553-554; 2pages.
Kendall, et al., "Multicentre randomised controlled trial of nasal diamorphine for analgesia in children and teenagers with clinical fractures", BMJ, 2001; pp. 261-265; 5pages.
Rey, et al., "Pharmacokinetics of midazolam in children: comparative study of intranasal and intravenous administration", Eur J Clin Pharmacol, 1991, pp. 355-357; 3pages.
Henderson, et al., "Pre-induction of anesthesia in pediatric patients with nasally administered sufentanil", Anesthesiology, 1988, pp. 671-675; 5pages.
Karl, et al., "Comparison of the safety and efficacy of intranasal midazolam or sufentanil for preinduction of anesthesia in pediatric patients", Anesthesiology, 1992, pp. 209-215; 7pages.
Abrams, et al., "Safety and effectiveness of intranasal administration of sedative medications (ketamine, midazolam, or sufentanil) for urgent brief pediatric dental procedures", Anesth Prog, 1993, pp. 63-66; 4pages.
Zedie, et al., "Comparison of intranasal midazolam and sufentanil premedication in pediatric outpatients", Clin Pharmacol Ther, 1996, pp. 341-3488; 8pages.
Weber, et al., "Premedication with nasal s-ketamine and midazolam provides good conditions for induction of anesthesia in preschool children", Can J Anaesth, 2003, pp. 470-475; 6pages.
Weksler, et al., "Nasal ketamine for paediatric premedication", Can J Anaesth, 1993, pp. 119-121; 3pages.
Diaz, "Intranasal ketamine preinduction of paediatric outpatients", Paediatr Anaesth, 1997, pp. 273-278; 6pages.
Roelofse, et al., "Intranasal sufentanil/midazolam versus ketamine/midazolam for analgesia/sedation in the pediatric population prior to undergoing multiple dental extractions under general anesthesia: a prospective, double-blind, randomized comparison", Anesth Prog, 2004, pp. 114-121; 8pages.
Drover, et al., "The pharmacokinetics of ketorolac after single postoperative intranasal administration in adolescent patients", Anesth Analg, 2012, pp. 1270-1276; 7pages.
Borland, et al., "A randomized controlled trial comparing intranasal fentanyl to intravenous morphine for managing acute pain in children in the emergency department", Ann Emerg Med, 2007, pp. 335-340; 6pages.
Nielsen, et al., "Intranasal Sufentanil / Ketamine analgesia in children", Pediatric Anesthesia, 2014, pp. 170-180; 11pages.

* cited by examiner

*Primary Examiner* — Jeffrey S Lundgren
*Assistant Examiner* — Ibrahim D Bori
(74) *Attorney, Agent, or Firm* — Maier & Maier, PLLC

(57) ABSTRACT

An aqueous composition for intranasal administration by spray including a mixture of (a) sufentanil, a salt and/or analogs thereof and (b) ketamine, a salt and analogs thereof in solution. Also, an aqueous composition for intranasal administration by spray including (a) sufentanil, a salt and/or analogs thereof in solution and an aqueous composition for intranasal administration by spray including (b) ketamine, a salt and/or analogs thereof in solution, for use in a method for the treatment or prevention of pain in a child. The composition is useful for treating or preventing pain in a child of 17 years or younger. The composition is delivered from a nasal spray device to treat or prevent the pain such as procedural pain in a child.

15 Claims, No Drawings

PEDIATRIC COMBINATION

CROSS-REFERENCE TO RELATED APPLICATIONS

The present patent application claims benefit and priority to European Application No. 19204617.5 filed on Oct. 22, 2019, which is hereby incorporated by reference into the present disclosure.

FIELD

The present invention relates to an aqueous composition for intranasal administration by spray comprising (a) sufentanil, a salt and/or analogs thereof in solution and an aqueous composition for intranasal administration by spray comprising (b) ketamine, a salt and/or analogs thereof in solution. The combination of these compositions is useful in a method for the treatment or prevention of pain in a child. In particular the aqueous composition is for use in a method for the treatment or prevention of pain in a child and is administered by a nasal spray device. The present invention furthermore relates to a pre-filled and ready to use nasal spray device, a kit of parts, and an emergency vehicle comprising the nasal spray device or kit of parts. The present invention also relates to a method of treating or preventing pain in a child.

BACKGROUND

Children attending hospital experience painful procedures that can leave lasting negative impressions. Procedures range from a simple venipuncture to the more invasive removal of drainage tubes and burn dressings. Children who have once experienced procedural pain are more likely to have increased pain during future painful procedures (Blount et al). Furthermore, procedural pain in the pediatric population is often underestimated and undertreated (Blount et al). Pharmacological management includes several drug options e.g. opioids, nitrous oxide, topical anesthetics. However, pediatric formulations that permit accurate dosing and are accepted by children are often lacking.

Intranasal administration provides direct access to the systemic circulation and may be an acceptable route of administration for children (Hadley et al and Kendall et al). In children, intranasal midazolam (Rey et al), sufentanil (Henderson et all; Karl et al; Abrams et al; and Zedie et al) and ketamine (Abrams et al; Weber et al; Weksler et al; and Diaz et al) have been used for preinduction of anesthesia and combinations of sufentanil/midazolam or ketamine/midazolam for preinduction of anesthesia and postoperative analgesia (Roelofse et al). The analgesic effect of intranasal ketorolac (Drover et al), diamorphine (Kendall et al) and fentanyl (Borland et al) has been investigated in children.

In Nielsen et al, Pedeatric Anesthesia 24 (2014), "Intranasal Sufentanil/Ketamine analgesia in children", p. 170-180, it is stated that pediatric formulations that permit accurate dosing, are accepted by children and a have a rapid onset of analgesia are lacking. The authors concluded that sufenta-nil/ketamine nasal spray provided rapid onset of analgesia for a variety of painful procedures with mild side-effects and has promising features for use in pediatric procedural pain management.

US2004092531 describes an active substance combination that contains as the active substance component a) at least one opioid compound that has a fentanyl-type structure and/or the enantiomers and/or the diastereomers thereof and/or at least one corresponding pharmaceutically acceptable salt, and as the active substance component b) ketamine and/or at least one of its physiologically acceptable salts. The weight ratio of active substance component a) to active substance component b) ranges from 1:20 to 1:1500. The invention also relates to medicament formulations and medicaments that contain the inventive active substance combination and to the use of said active substance combination for producing medicaments. There do not appear to be any disclosure of the combined use of sufentanil and ketamine in low dosage and for treatment of pain by intranasal delivery in children.

U.S. Pat. No. 6,825,203 describes a topical pharmaceutical composition, formulated with at least one local anesthetic and at least one opioid analgesic, and methods of providing pain relief to a subject through topical administration of the composition in an amount and a duration sufficient to synergistically potentiate an antinociceptive response. In particular, disclosed is a topical pharmaceutical composition comprising i) a topical dosage form selected from the group consisting of a gel, lotion, cream, oil, emulsion and ointment and ii) synergistically effective amounts of morphine and lidocaine, wherein the morphine to lidocaine ratio is about 1:0.1 to about 1:2.4, and morphine is in an amount ranging from about 0.01% to about 25%, and lidocaine is in amount ranging from about 0.01% to about 25%. There do not appear to be any disclosure of the combined use of sufentanil and ketamine in low dosage and for treatment of pain by intranasal delivery in children.

SUMMARY

The present inventors have experienced that there is an unmet medical need for treatment or prevention of pain, in particular procedural pain, in children 17 years of age or younger. None of the available drugs and/or administration routes is considered sufficient and in many ways does not actually solve the pain issue in children. In particular the problem of relieving pain in children that are in acute need of pain treatment, but not close to a facility, such as a hospital, or a physician who have access to pain relieving medicine, has been identified and solved. Additionally, the present combination has fast on-set of therapeutic effect and is needle free. Moreover, administration of pain relieving medicine to children, in particular small children under age 2, usually requires an authorized practitioner, such as a physician, to be in charge of or at least supervising or monitoring administration of pain relieving medicine, such as any of the above described medicines and administration routes, even in ambulatory and emergency settings. The present combination is easy to administer and is absorbed directly to the systemic blood supply, avoiding hepatic first-pass metabolism. Furthermore, the dose is titratable.

The present invention concerns in one aspect an aqueous composition for intranasal administration by spray comprising a mixture of (a) sufentanil, a salt and/or analogs thereof and (b) ketamine, a salt and/or analogs thereof in solution. Preferably, (a) is sufentanil, such as sufentanil citrate and (b) is ketamine, such as ketamine hydrochloride. Typically, (a) and (b) are present in a weight ratio (a):(b) from 1:5000 to 1:500, wherein the weight of (a) and (b) are calculated on the free compounds. The aqueous solution usually has a total volume from 25 µl to 5 ml, and the solution contains a buffer, such as a phosphate buffer, maintaining pH from 4-8, such as 4-6 or 5-7. Sufentanil calculated as the free base is present in a concentration of 25-200 µg/ml and ketamine calculated as the free base is present in a concentration of 25-200 mg/ml. The aqueous solution is preferably sterile or a preservative has been added to the composition.

In a further aspect the present invention relates to the composition as described above for use in a method for the treatment or prevention of pain in a child. The composition is administered via a nasal spray device. When administered to the child the dosage volume is from 0.05-0.5 ml, e.g. 0.05-0.1 ml, and typically 1 or 2 dosage volume(s) is/are administered to alleviate the pain. The children are preferably under 18 years, and the present invention is efficient for children under 2 years or even under 1 year. Children may differ in weight, but the present invention is efficient for children who weigh below 60 kg.

In a still further aspect the present invention relates to a pre-filled and ready to use nasal spray device comprising an aqueous composition for intranasal administration by spray comprising a mixture of (a) sufentanil, a salt and/or analogs thereof and (b) ketamine, a salt and/or analogs thereof in solution, such as any one of the composition embodiments described above. In particular, the pre-filled and ready to use nasal spray device is suitable for use in an emergency vehicle, such as an ambulance, and may be handled by a paramedic. When present in an emergency vehicle the pre-filled and ready to use nasal spray device is pre-assembled and included in a kit of parts together with a packing.

In a further aspect the present invention relates to a kit of parts comprising the pre-filled and ready to use nasal spray device as described above and a packing.

The pre-filled and ready to use nasal spray device or the kit of parts as described above may also be contained in an emergency vehicle, such as an ambulance and may be handled by a paramedic without supervision of a physician.

In a still further aspect the present invention relates to a method of treating or preventing pain in a child comprising administering to said child an effective dosage of the aqueous composition for intranasal administration by spray comprising a mixture of (a) sufentanil, a salt and/or analogs thereof and (b) ketamine, a salt and/or analogs thereof in solution from a pre-filled and ready to use nasal spray device. In particular, the pre-filled and ready to use nasal spray device is located in an emergency vehicle, typically an ambulance.

In a further aspect the present invention relates to an aqueous composition for intranasal administration by spray comprising (a) sufentanil, a salt and/or analogs thereof in solution and (b) ketamine, a salt and/or analogs thereof in solution for use in a method for the treatment or prevention of pain in a child.

In a still further aspect the present invention relates to a pre-filled and ready to use nasal spray device comprising the composition of the present invention.

In a further aspect the present invention relates to a pre-filled and ready to use nasal spray device comprising the composition of the present invention for use in an emergency vehicle, such as an ambulance.

In a still further aspect the present invention relates to a kit of parts comprising the pre-filled and ready to use nasal spray device comprising the composition of the present invention and a packing.

In a further aspect the present invention relates to an emergency vehicle comprising the pre-filled and ready to use nasal spray device comprising the composition of the present invention or the kit of parts comprising the pre-filled and ready to use nasal spray device comprising the composition of the present invention and a packing.

In a still further aspect the present invention relates to a method of treating or preventing pain in a child comprising administering to said child an effective dosage of the composition of the present invention from the pre-filled and ready to use nasal spray device comprising the composition of the present invention.

DETAILED DESCRIPTION

In a broad aspect, the present invention concerns an aqueous composition for intranasal administration by spray comprising a mixture of (a) sufentanil, a salt and/or analogs thereof and (b) ketamine, a salt and/or analogs thereof in solution.

As used herein the term "aqueous composition" means a liquid composition wherein the carrier is water, such as sterile water. Other additive(s) that may be necessary, dependent on the medicinal drug(s) to be dissolved herein may be added such as solubility enhancer(s), preservative(s), etc.

As used herein the term "intranasal administration by spray" means administration of an aqueous composition, such as the above mixture of (a) and (b) in solution or (a) in solution and (b) in solution and from separate containers, to a nostril of a human subject through a means for spraying, such as a nozzle or tip capable of blowing the composition as small droplets into the nostril.

As used herein the term "a mixture of (a) sufentanil, a salt and/or analogs thereof and (b) ketamine, a salt and/or analogs thereof in solution" means that (a) and (b) are blended together and dissolved in water. Therefor the solution contains both (a) and (b), but not (a) in one solution and (b) in a different solution.

As used herein the term "(a) sufentanil, a salt and/or analogs thereof" means sufentanil, a salt of sufentanil, an analog of sufentanil or an analog of a salt of sufentanil, or a mixture of two or more thereof. Sufentanil has the systematic (IUPAC) name N-[4-(methoxymethyl)-1-(2-thiofuran-2-ylethyl)-4-piperidyl]-N-phenylpropanamide and is a well-known drug for pain relief. A salt of sufentanil may be any acid salt, such as inorganic or organic salts, and is preferably a pharmaceutically acceptable acid addition salt, such as a citrate. An analog of sufentanil or a salt thereof is a compound having a pain relieving effect similar to sufentanil. One analog of sufentanil is fentanyl that has the systematic (IUPAC) name N-(1-(2-phenylethyl)-4-piperidinyl)-N-phenylpropanamide and is a well-known drug for pain relief. Another analog of sufentanil is alfentanil that has the systematic (IUPAC) name N-{1-[2-(4-ethyl-5-oxo-4,5-dihydro-1H-1,2,3,4-tetrazol-1-yl)ethyl]-4-(methoxymethyl) piperidin-4-yl}-N-phenylpropanamide and is a well-known drug for pain relief. Solvates such as hydrates of the above compounds or salts are also to be understood as comprised in the term.

As used herein the term "(b) ketamine, a salt and/or analogs thereof" means ketamine, a salt of ketamine, an analog of ketamine or an analog of a salt of ketamine, or a mixture of two or more thereof. Ketamine has the systematic (IUPAC) name (RS)-2-(2-Chlorophenyl)-2-(methylamino) cyclohexanone and is a well-known anesthetic and analgesic. A salt of ketamine may be any acid salt, such as inorganic or organic salts, and is preferably a pharmaceutically acceptable acid addition salt, such as a hydrochloride. An analog of ketamine or a salt thereof is a compound having an anesthetic effect similar to ketamine. One analog of ketamine is S-ketamine that has the systematic (IUPAC) name (S)-2-(2-Chlorophenyl)-2-(methylamino) cyclohexanone and is a well-known anesthetic. Solvates such as hydrates of the above compounds or salts are also to be understood and comprised in the term.

In one embodiment (a) and (b) are present in a weight ratio (a):(b) from 1:5000 to 1:500, wherein the weight of (a) and (b) are calculated on the free compounds. In a further embodiment the weight ratio (a):(b) is about 1:4000 to 1:750. In another embodiment the weight ratio (a):(b) is about 1:2000 to 1:750. Typically, the weight ratio (a):(b) is about 1:1000.

In a further embodiment (a) is sufentanil or a salt thereof. Typically, (a) is a pharmaceutically acceptable acid addition salt of sufentanil. Preferably, (a) is sufentanil citrate.

In a still further embodiment (a) is fentanyl or a salt thereof. Typically, (a) is a pharmaceutically acceptable acid addition salt of fentanyl. Preferably, (a) is fentanyl citrate.

In a further embodiment (a) is alfentanil or a salt thereof. Typically, (a) is a pharmaceutically acceptable acid addition salt of alfentanil. Preferably, (a) is alfentanil hydrochloride.

In a still further embodiment (b) is ketamine or a salt thereof. Typically, (b) is a pharmaceutically acceptable acid addition salt of ketamine. Preferably, (b) is ketamine hydrochloride.

In a further embodiment (b) is S-ketamine or a salt thereof. Typically, (b) is a pharmaceutically acceptable acid addition salt of S-ketamine. Preferably, (b) is S-ketamine hydrochloride.

In a still further embodiment the composition of the present invention has a volume from 25 µl to 5 ml, such as a volume from 50 µl to 5 ml. Typically, the volume is from 0.1 to 2 ml. Preferably, the volume is from 0.5 to 2 ml, such as 1 ml.

As used herein the term "a volume" means the total volume of liquid water, dissolved compounds, such as sufentanil and ketamine, and optionally additives dissolved therein, such as a buffer. Thus, any undissolved compound or other additive is not considered part of the volume.

In a further embodiment the solution contains a buffer. The buffer is able to maintain pH at a constant level, such as a pH between 4 and 8. Thus, e.g. pH may be 4, 4.5, 5, 5.5, 6, 6.5, 7, 7.5 or 8, typically 5.5-6.5, such as about 4-6. The buffer may be any suitable buffer, such as a phosphate buffer or a Citric acid buffer.

In a still further embodiment the concentration of (a) is 25-200 µg/ml. Typically, the concentration of (a) is 40-150 µg/ml, such as 40-100 µg/ml, e.g. 50-70 µg/ml. In a further embodiment the concentration of (a) is 65-85 µg/ml. In a still further embodiment the concentration of (a) is 80-100 µg/ml. In a further embodiment the concentration of (a) is 140-160 µg/ml.

In a further embodiment the concentration of (b) is 25-200 mg/ml. Typically, the concentration of (b) is 40-150 mg/ml, such as 40-100 mg/ml, e.g. 50-70 mg/ml. In a further embodiment the concentration of (b) is 65-85 mg/ml. In a still further embodiment the concentration of (b) is 80-100 mg/ml. In a further embodiment the concentration of (b) is 140-160 mg/ml.

In a still further embodiment the composition of the present invention further comprises an additional pharmaceutically acceptable additive, such as a preservative. Alternatively, the composition of the present invention may also be sterilized, so as to provide a sterile composition.

In a further aspect the present invention relates to an aqueous composition for intranasal administration by spray comprising a mixture of (a) sufentanil, a salt and/or analogs thereof and (b) ketamine, a salt and/or analogs thereof in solution, for use in a method for the treatment or prevention of pain in a child. The above described embodiments for the composition also apply for this aspect. In a further embodiment the composition is administered via a nasal spray device, such as a pre-filled and ready to use nasal spray device. In a still further embodiment a dosage volume of 0.05-0.5 ml is administered to a nostril of a human subject. Typically, the dosage volume is 0.05-0.1 ml. In a further embodiment the dosage volume of 0.05-0.3 ml is administered one time. In another embodiment the dosage volume of 0.05-0.3 ml is administered two times, typically with 10 minutes apart in each nostril. In a still further embodiment the composition of the present invention is for use in a method for the prevention of pain in a child. In a further embodiment the pain is procedural pain. In a still further embodiment the pain is acute pain. In a further embodiment the pain is procedural and acute pain. In a still further embodiment the child is 17 years or younger. In a particular embodiment the child is under 2 years, such as under 1 year, e.g. 3-6 months. In a further embodiment the child weighs below 60 kg. In some instances the children weighs below 50 kg, such as below 35 kg, below 25 kg, below 10 kg, all of which constitutes individual embodiments of the present invention.

As used herein the term "nasal spray device" means any device adapted for spraying a liquid solution into a nostril of a human subject which device is air tight when assembled. In particular and as used herein "a pre-filled and ready to use nasal spray device" means a nasal spray device having a body part containing a composition of the present invention and a pump system with a nozzle or other spray function for administration via the nasal delivery route, and this device is typically assembled (ia. pre-assembled) and ready for use in a human subject, in particular a child. Furthermore, "a pre-filled and ready to use nasal spray device" means that the nasal spray device containing the composition of the present invention can be stored for a sufficient period of time, such as 1 month, 3 months or one year, and is ready to be used by e.g., a paramedic in an ambulance. This device can be used for instance, by a paramedic and does not require an authorized practitioner, such as a physician. The device may also be a kit of parts comprising a body part holding the composition of the present invention e.g., a glass bottle with a thread or snapping means and a pump system for spraying, wherein said pump system is adapted to provide a nasal spray device which is sealed and airtight and can be stored. An example of such a pump system for use as part of the device is available from Aptar Pharma a part of the Aptar Group, such as a CPS vented dip tube (a versatile spray pump). The Aptar Group owns intellectual property to these suitable pump systems for intranasal delivery. For instance, the body part may be a container in glass, and may consist of one chamber holding a solution of a mixture of (a) and (b) or two separate chambers one holding (a) in solution and the other holding (b) in solution.

As used herein the term "a dosage volume" means the liquid dosage volume containing the composition comprising water and active compounds, such as sufentanil and ketamine, delivered from the device to a nostril. The typical dosage volume is form 0.05-0.5 ml, e.g. 0.05-0.1 ml.

As used herein the term "pain in a child" means pain of any origin in a child of age 17 years or younger. Preferably the pain is procedural pain or acute pain or both. Examples of procedural pain are: pain caused by medical or diagnostic procedures e.g. blood sampling, placement of peripheral venous access, placement of naso-gastric tube, fracture reposition, suturing of minor laceration, removal of chest drain or other drains. Examples of acute pain are: acute pain in children and adolescent from 1 to under 18 years in a hospital or prehospital setting, surgical pain, dental pain, burn pain, pain caused by medical or diagnostic procedures and pain caused by traumatic injury in the prehospital setting.

As used herein the term "treatment" and "treating" as used herein means the management and care of a child subject for the purpose of combating a pain, such as a procedural and/or acute pain. The term is intended to include the full spectrum of treatments for a given condition from which the patient is suffering, such as administration of the active compounds to alleviate the pain, in particular procedural or acute pain or both as well as to prevent the pain, wherein prevention is to be understood as the management and care of a child subject for the purpose of alleviating or removing the pain and includes the administration of the active compounds to prevent the onset of the pain.

In a further aspect the present invention relates to a pre-filled and ready to use nasal spray device comprising an aqueous composition for intranasal administration by spray comprising a mixture of (a) sufentanil, a salt and/or analogs thereof and (b) ketamine, a salt and/or analogs thereof in solution. The above described embodiments for the composition also apply for this aspect. In a further embodiment the pre-filled and ready to use nasal spray device of the present invention is for use in an emergency vehicle, such as an ambulance.

In a further aspect the present invention relates to a kit of parts comprising the pre-filled and ready to use nasal spray device comprising an aqueous composition for intranasal administration by spray comprising a mixture of (a) sufentanil, a salt and/or analogs thereof and (b) ketamine, a salt and/or analogs thereof in solution and a packing. The above described embodiments for the composition also apply for this aspect.

In a further aspect the present invention relates to an emergency vehicle comprising the pre-filled and ready to use nasal spray device comprising an aqueous composition for intranasal administration by spray comprising a mixture of (a) sufentanil, a salt and/or analogs thereof and (b) ketamine, a salt and/or analogs thereof in solution and optionally a packing. The above described embodiments for the composition also apply for this aspect.

In a further aspect the present invention relates to a method of treating or preventing pain in a child comprising administering to said child an effective dosage of an aqueous composition for intranasal administration by spray comprising a mixture of (a) sufentanil, a salt and/or analogs thereof and (b) ketamine, a salt and/or analogs thereof in solution from a pre-filled and ready to use nasal spray device of the present invention. In a further embodiment the pre-filled and ready to use nasal spray device comprising an aqueous composition for intranasal administration by spray comprising a mixture of (a) sufentanil, a salt and/or analogs thereof and (b) ketamine, a salt and/or analogs thereof in solution is located in an emergency vehicle, such as an ambulance. In a still further embodiment the pre-filled and ready to use nasal spray device comprising an aqueous composition for intranasal administration by spray comprising a mixture of (a) sufentanil, a salt and/or analogs thereof and (b) ketamine, a salt and/or analogs thereof in solution is handled by a paramedic. The above described embodiments for the composition also apply for this aspect.

In a further aspect the present invention relates to an aqueous composition for intranasal administration by spray comprising (a) sufentanil, a salt and/or analogs thereof in solution. In an embodiment (a) is sufentanil or a salt thereof. Typically, (a) is a pharmaceutically acceptable acid addition salt of sufentanil. Preferably, (a) is sufentanil citrate. In a still further embodiment (a) is fentanyl or a salt thereof. Typically, (a) is a pharmaceutically acceptable acid addition salt of fentanyl. Preferably, (a) is fentanyl citrate. In a further embodiment (a) is alfentanil or a salt thereof. Typically, (a) is a pharmaceutically acceptable acid addition salt of alfentanil. Preferably, (a) is alfentanil hydrochloride. In a still further embodiment the composition of the present invention has a volume from 25 µl to 5 ml. Typically, the volume is from 0.1 to 2 ml. Preferably, the volume is from 0.5 to 2 ml, such as 1 ml. In a further embodiment the solution contains a buffer. The buffer is able to maintain pH at a constant level, such as a pH between 4 and 8. Thus, e.g. pH may be 4, 4.5, 5, 5.5, 6, 6.5, 7, 7.5 or 8, typically 5.0-6.5, such as about 6. The buffer may be any suitable buffer, such as a phosphate buffer or a Citric acid buffer. In a still further embodiment the concentration of (a) is 25-200 µg/ml. Typically, the concentration of (a) is 40-150 µg/ml, such as 40-100 µg/ml, e.g. 50-70 µg/ml. In a further embodiment the concentration of (a) is 65-85 µg/ml. In a still further embodiment the concentration of (a) is 80-100 µg/ml. In a further embodiment the concentration of (a) is 140-160 µg/ml. In a still further embodiment the composition of the present invention further comprises an additional pharmaceutically acceptable additive, such as a preservative. Alternatively, the composition of the present invention may also be sterilized, so as to provide a sterile composition.

In a further aspect the present invention relates to an aqueous composition for intranasal administration by spray comprising (b) ketamine, a salt and/or analogs thereof in solution. In an embodiment (b) is ketamine or a salt thereof. Typically, (b) is a pharmaceutically acceptable acid addition salt of ketamine. Preferably, (b) is ketamine hydrochloride. In a further embodiment (b) is S-ketamine or a salt thereof. Typically, (b) is a pharmaceutically acceptable acid addition salt of S-ketamine. Preferably, (b) is S-ketamine hydrochloride. In a still further embodiment the composition of the present invention has a volume from 25 µl to 5 ml. Typically, the volume is from 0.1 to 2 ml. Preferably, the volume is from 0.5 to 2 ml, such as 1 ml. In a further embodiment the solution contains a buffer. The buffer is able to maintain pH at a constant level, such as a pH between 4 and 8. Thus, e.g. pH may be 4, 4.5, 5, 5.5, 6, 6.5, 7, 7.5 or 8, typically 5.0-6.5, such as about 6. The buffer may be any suitable buffer, such as a phosphate buffer or a Citric acid buffer. In a further embodiment the concentration of (b) is 25-200 mg/ml. Typically, the concentration of (b) is 40-150 µg/ml, such as 40-100 µg/ml, e.g. 50-70 µg/ml. In a further embodiment the concentration of (b) is 65-85 mg/ml. In a still further embodiment the concentration of (b) is 80-100 mg/ml. In a further embodiment the concentration of (b) is 140-160 mg/ml. In a still further embodiment the composition of the present invention further comprises an additional pharmaceutically acceptable additive, such as a preservative. Alternatively, the composition of the present invention may also be sterilized, so as to provide a sterile composition.

In a broader aspect the present invention concerns an aqueous composition for intranasal administration by spray comprising (a) sufentanil, a salt and/or analogs thereof in solution and an aqueous composition for intranasal administration by spray comprising (b) ketamine, a salt and/or analogs thereof in solution, for use in a method for the treatment or prevention of pain in a child.

It should be clear that even though the experiments herein are carried out by using a mixture of (a) and (b) in solution, such mixture can take place after (a) and (b) leaves the spray for intranasal delivery or can take place in a mixer chamber as part of a device for intranasal administration by spray, or can even take place from separate nasal spray devices wherein one contains (a) and another contains (b).

In an embodiment the compositions are administered via a pre-filled and ready to use nasal spray device. In a further embodiment the device comprises a first chamber for (a) and a second chamber for (b). In a still further embodiment the device comprises a further chamber for mixing (a) and (b) before intranasal administration by spray. In another embodiment the device is constructed to deliver (a) and (b) separately and simultaneously by intranasal administration by spray.

The above described embodiments for the aqueous composition comprising (a) or (b) also apply for this aspect. In a further embodiment the compositions are administered via a nasal spray device, such as a pre-filled and ready to use nasal spray device, typically, a pre-assembled, pre-filled and ready to use nasal spray device.

In a still further embodiment a dosage volume of 0.05-0.5 ml containing (a) and a dosage volume of 0.05-0.5 ml containing (b) are administered to a nostril of a human subject. Typically, the dosage volume is 0.05-0.3 ml containing (a). Typically, the dosage volume is 0.05-0.3 ml containing (b). In a further embodiment the dosage volume of 0.05-0.1 ml containing (a) and the dosage volume of 0.05-0.1 ml containing (b) are administered one time. In another embodiment the dosage volume of 0.05-0.1 ml containing (a) and the dosage volume of 0.05-0.1 ml containing (b) are administered two times, typically with 10 minutes apart in each nostril. In a still further embodiment the composition of the present invention is for use in a method for the prevention of pain in a child. In a further embodiment the pain is procedural pain. In a still further embodiment the pain is acute pain. In a further embodiment the pain is procedural and acute pain. In a still further embodiment the child is 17 years or younger, such as under 17 years. In a particular embodiment the child is under 2 years, such as under 1 year, e.g. 3-6 months. In a further embodiment the child weighs below 60 kg. In some instances the children weighs below 50 kg, such as below 35 kg, below 25 kg, below 10 kg, all of which constitutes individual embodiments of the present invention.

In a still further aspect the present invention concerns a pre-filled and ready to use nasal spray device comprising an aqueous composition for intranasal administration by spray comprising (a) sufentanil, a salt and/or analogs thereof in solution and an aqueous composition for intranasal administration by spray comprising (b) ketamine, a salt and/or analogs thereof in solution. In an embodiment pre-filled and ready to use nasal spray device is for use in an emergency vehicle, such as an ambulance. The above described embodiments for the compositions also apply for this aspect.

In a further aspect the present invention concerns a kit of parts comprising the pre-filled and ready to use nasal spray device of the present invention and a packing. The above described embodiments for the compositions also apply for this aspect.

In a still further aspect the present invention relates to an emergency vehicle comprising the pre-filled and ready to use nasal spray device of the present invention or the kit of parts of the present invention. The above described embodiments for the compositions also apply for this aspect.

In a further aspect the present invention relates to a method of treating or preventing pain in a child comprising administering to said child an effective dosage of an aqueous composition for intranasal administration by spray comprising (a) sufentanil, a salt and/or analogs thereof in solution and an aqueous composition for intranasal administration by spray comprising (b) ketamine, a salt and/or analogs thereof in solution, from the pre-filled and ready to use nasal spray device of the present invention. In an embodiment the pre-filled and ready to use nasal spray device of the present invention is located in an emergency vehicle. In a further embodiment the pre-filled and ready to use nasal spray device of the present invention is handled by a paramedic.

Further embodiments of the process are described in the experimental section herein, and each individual process as well as each starting material constitutes embodiments that may form part of embodiments.

The above embodiments should be seen as referring to any one of the aspects (such as 'method for treatment', 'pharmaceutical composition', or 'composition for use in a method') described herein as well as any one of the embodiments described herein unless it is specified that an embodiment relates to a certain aspect or aspects of the present invention.

All references, including publications, patent applications and patents, cited herein are hereby incorporated by reference to the same extent as if each reference was individually and specifically indicated to be incorporated by reference and was set forth in its entirety herein.

All headings and sub-headings are used herein for convenience only and should not be construed as limiting the invention in any way.

Any combination of the above-described elements in all possible variations thereof is encompassed by the invention unless otherwise indicated herein or otherwise clearly contradicted by context.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also pro-vide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

This invention includes all modifications and equivalents of the subject matter recited in the aspects or claims presented herein to the maximum extent permitted by applicable law.

The present invention is further illustrated by the following examples that, however, are not to be construed as limiting the scope of protection. The features disclosed in the foregoing description and in the following examples may, both separately and in any combination thereof, be material for realizing the invention in diverse forms thereof.

Experimental

Four different strengths/concentrations of the formulation to be used in clinical trials are prepared. An aqueous composition of (a) sufentanil and (b) ketamine in a phosphate buffer is prepared by 1) (c) dissolution of $NaH_2PO_4$ and $Na_2HPO_4$ in purified water, followed by sterilization in an autoclave with high pressure saturated steam at 121° C. (249° F.), 2) the relevant content of (a) and (b) are dissolved in (c), (d) the dissolution of (a)+(b)+(c) is filtered through a 0.22 μm filter and filled into vials or bottles of the nasal spray device. The container closure system used for the product is a mechanical multi dose nasal spray device. It consists of a vented pump (nasal spray device from Aptar Pharma (or equivalent) and a paediatric actuator mounted on a 3 ml glass v-bottom bottle (u-save bottle "SGD Pharma" or equivalent). The dosing volume of the pump is 100 microliters. This intranasal formulation (d) is used in a clinical trial with 50 paediatric patients 1-18 years. The trial is designed to investigate pharmacokinetics, analgesic effect and safety of the intranasal formulation (d) for procedural pain in children by use of the nasal spray device from Aptar Pharma. A pre-filled and ready to use nasal spray in two strengths/concentrations with a pump dosing volume of 50 or 100 microliters (Table 1) will be tested during clinical development, including the following planned clinical studies in which (d) will be used: 1) a safety, feasibility and efficacy study including 300 paediatric patients 1-18 years in the prehospital setting. In this study a single dose of intranasal sufentanil/ketamine, target dose sufentanil 0.5 μg/kg and ketamine 0.5 mg/kg is administered and dose can be repeated after 10-15 min if sufficient analgesia is not achieved. 2) A supplemental safety study is ongoing to assess safety and tolerability of intranasal sufentanil/ketamine using retrospective data from 10 years of routine clinical care in children 1-17 years needing analgesia/sedation with sufentanil and/or s-ketamine solution for injection administered intranasally for procedural pain/sedation. In this non-intervention study data from approximately 3000 medical procedures are available and the dose of intranasal sufentanil is approx. 0.5 μg/kg and/or s-ketamine approx. 0.5 mg/kg. 3) A bioavailability study to assess absolute bioavailability of intranasal sufentanil/ketamine in 13 healthy volunteers. The study is designed as a randomised, open-label, single dose, 3-period crossover study with a dose of intranasal 10 μg sufentanil/10 mg ketamine, Intravenous sufentanil 10 μg or Intravenous ketamine 10 mg. 4) An efficacy, concentration-effect and dose-response study in 220 patients undergoing third molar extraction to assess the efficacy of the combination of intranasal sufentanil/ketamine versus intranasal sufentanil or intranasal ketamine or placebo and to assess the concentration-effect relationship. A randomized double-blinded four-arm (main interventions), two doses (separated by 1 hour) parallel-group design. 5) A pharmacokinetic study in 25 paediatric patients 1-2 years undergoing elective surgery and needing premedication before anaesthesia. In this open-label study a single dose of intranasal sufentanil/ketamine, target dose of intranasal sufentanil/ketamine of 0.5-0.7 μg/kg sufentanil and 0.5-0.7 mg/kg ketamine (target dose) is administered as premedication to assess pharmacokinetic parameter estimates in this age group.

TABLE 1

Sufentanil/ketamine fixed combination, solution 1 ml

| | 60 μg/60 mg Content | 90 μg/90 mg Content | Specification | Functionality |
|---|---|---|---|---|
| Sufentanil citrate (equivalent to sufentanil) | 90.00 μg (60 μg) | 135 μg (90 μg) | Ph. Eur | Drug substance |
| Ketamine Hydrochloride (equivalent to ketamine) | 69.19 mg (60 mg) | 103.79 mg (90 mg) | Ph. Eur | Drug substance |
| 0.1M $NaH_2PO_4$/$Na_2HPO_4$ buffer | Ad 1 ml | Ad 1 ml | Ph. Eur | Excipient |

REFERENCES

1) Blount R L, Piira T, Cohen L L, et al. Pediatric procedural pain. Behav Modif 2006; 30: 24-49
2) Hadley G, Maconochie I, Jackson A. A survey of intranasal medication use in the paediatric emergency setting in England and Wales. Emerg Med J 2010; 27: 553-554
3) Kendall J M, Reeves B C, Latter V S. Multicentre randomised controlled trial of nasal diamorphine for analgesia in children and teenagers with clinical fractures. BMJ 2001; 322: 261-265
4) Rey E, Delaunay L, Pons G, et al. Pharmacokinetics of midazolam in children: comparative study of intranasal and intravenous administration. Eur J Clin Pharmacol 1991; 41: 355-357
5) Henderson J M, Brodsky D A, Fisher D M, et al. Pre-induction of anesthesia in pediatric patients with nasally administered sufentanil. Anesthesiology 1988; 68: 671-675
6) Karl H W, Keifer A T, Rosenberger J L, et al. Comparison of the safety and efficacy of intranasal midazolam or sufentanil for preinduction of anesthesia in pediatric patients. Anesthesiology 1992; 76: 209-215
7) Abrams R, Morrison J E, Villasenor A, et al. Safety and effectiveness of intranasal administration of sedative medications (ketamine, midazolam, or sufentanil) for urgent brief pediatric dental procedures. Anesth Prog 1993; 40: 63-66
8) Zedie N, Amory D W, Wagner B K, et al. Comparison of intranasal midazolam and sufentanil premedication in pediatric outpatients. Clin Pharmacol Ther 1996; 59: 341-3488)
9) Weber F, Wulf H, el Saeidi G. Premedication with nasal s-ketamine and midazolam provides good conditions for induction of anaesthesia in preschool children. Can J Anaesth 2003; 50: 470-475
10) Weksler N, Ovadia L, Muati G, et al. Nasal ketamine for paediatric premedication. Can J Anaesth 1993; 40: 119-121

11) Diaz J H. Intranasal ketamine preinduction of paediatric outpatients. Paediatr Anaesth 1997; 7: 273-278
12) Roelofse J A, Shipton E A, de la Harpe C J, et al. Intranasal sufentanil/midazolam versus ketamine/midazolam for analgesia/sedation in the pediatric population prior to undergoing multiple dental extractions under general anesthesia: a prospective, double-blind, randomized comparison. Anesth Prog 2004; 51: 114-121
13) Drover D R, Hammer G B, Anderson B J. The pharmacokinetics of ketorolac after single postoperative intranasal administration in adolescent patients. Anesth Analg 2012; 114: 1270-1276
14) Borland M, Jacobs I, King B, et al. A randomized controlled trial comparing intranasal fentanyl to intravenous morphine for managing acute pain in children in the emergency department. Ann Emerg Med 2007; 49: 335-340
15) Nielsen et al, Pediatric Anesthesia 24 (2014), "Intranasal Sufentanil/Ketamine analgesia in children", p. 170-180

We claim:

1. A pre-filled and ready to use nasal spray device, comprising:
    an aqueous composition for intranasal administration by spray comprising a mixture of (a) sufentanil, or a salt thereof and (b) ketamine, or a salt thereof in solution wherein (a) and (b) are present in a weight ratio (a):(b) from 1:5000 to 1:500, wherein the weight of (a) and (b) are calculated based on the free compounds, and the solution contains a buffer maintaining pH from 4 to 5.5,
    wherein the pre-filled and ready to use nasal spray device is adapted to give a dosage volume of 0.05 to 0.1 ml of the composition per unit dose,
    wherein the prefilled and ready to use nasal spray device is sealed and airtight to provide storage of the aqueous composition for at least 3 months.

2. A method of treating or preventing pain in a child comprising administering to said child an effective dosage of the composition by spraying the composition from the pre-filled and ready to use nasal spray device of claim 1.

3. The method of claim 2, wherein the pain is acute pain.

4. The method of claim 2, wherein the pain selected from the group consisting of surgical pain, dental pain, burn pain, pain caused by medical or diagnostic procedures, pain caused by traumatic injury in a prehospital setting, and acute pain in children and adolescent from 1 to under 18 years in a hospital or prehospital setting.

5. The device of claim 1, wherein the mixture is (a) sufentanil citrate and (b) ketamine hydrochloride.

6. The device of claim 1, having a volume from 25 µl to 5 ml.

7. The device of claim 1, wherein the solution pH is from 4.5 to 5.5.

8. The device of claim 7, wherein the buffer is selected from a phosphate buffer or a citric acid buffer.

9. The device of claim 1, wherein the pre-filled and ready to use nasal spray device is sealed and airtight to provide storage of the aqueous composition for 1 year.

10. The device of claim 1, wherein the concentration of (a) is 60 µg/ml and (b) is 60 mg/ml and the nasal spray device is adapted to give a dosage volume of 0.05 ml per unit dose.

11. The device of claim 1, wherein the concentration of (a) is 90 µg/ml and (b) is 90 mg/ml and the nasal spray device is adapted to give a dosage volume of 0.05 ml per unit dose.

12. The device of claim 1, wherein the concentration of (a) is 60 µg/ml and (b) is 60 mg/ml and the nasal spray device is adapted to give a dosage volume of 0.1 ml per unit dose.

13. The device of claim 1, wherein the concentration of (a) is 90 µg/ml and (b) is 90 mg/ml and the nasal spray device is adapted to give a dosage volume of 0.1 ml per unit dose.

14. The device of claim 1, wherein the aqueous composition further comprises an additional pharmaceutically acceptable additive.

15. The device of claim 14, wherein the pharmaceutically acceptable additive of the aqueous composition is a preservative.

* * * * *